United States Patent [19]

Schneider et al.

[11] 4,126,605

[45] Nov. 21, 1978

[54] PROCESS OF IMPROVING THE COMPATIBILITY OF GAMMA GLOBULINS

[75] Inventors: Waldemar Schneider; Dietrich Wolter, both of Hagen, Fed. Rep. of Germany

[73] Assignee: Plasmesco AG, Switzerland

[21] Appl. No.: 801,860

[22] Filed: May 31, 1977

Related U.S. Application Data

[63] Continuation-in-part of Ser. No. 644,749, Dec. 29, 1975, abandoned.

[51] Int. Cl.² .................. C07G 7/00; A61K 39/00; A61K 35/16
[52] U.S. Cl. .................. 260/112 B; 424/85; 424/101
[58] Field of Search .................. 260/112 B; 424/101, 424/85

[56] References Cited

U.S. PATENT DOCUMENTS

| | | | |
|---|---|---|---|
| 3,880,989 | 4/1975 | Garcia | 260/112 B |
| 3,956,259 | 5/1976 | Garcia et al. | 260/112 B |

*Primary Examiner*—Sam Rosen
*Attorney, Agent, or Firm*—Fitch, Even, Tabin & Luedeka

[57] ABSTRACT

A process for providing gamma globulin with improved intravenous compatibility. In the process, gamma globulin precipitated from blood or blood products is dissolved in an aqueous solution containing a hydrocolloid. The hydrocolloid is capable of forming a lyophilic sol. Gamma globulin is then precipitated from the solution to provide gamma globulin having improved intravenous compatibility.

20 Claims, 2 Drawing Figures

PROCESS OF IMPROVING THE COMPATIBILITY OF GAMMA GLOBULINS

The present application is a continuation-in-part of application Ser. No. 644,749, filed on Dec. 29, 1975, now abandoned.

The present invention relates to a process for preparing gamma globulin of high purity. More particularly, the present invention relates to the process for preparing gamma globulin having improved utility for intravenous administration.

Blood is a fluid which comprises solid components suspended in a liquid carrier. The solid components include the red and white blood corpuscles as well as the blood platelets or thrombocytes. The liquid carrier, or plasma, contains about 90 percent water and 10 percent solids. The solids dissolved in the plasma include gamma globulin. Gamma globulin is a protein which is used for the therapy and prophylaxis of infections. To provide a gamma globulin useful for intravenous administration, the other solids contained in the plasma must be separated from the gamma globulin to provide as pure a gamma globulin fraction as possible.

A particular process for the precipitation and isolation of gamma globulin from blood is known by the name "Cohn-Method" (Cohn et al, J. Amer. Chem. Soc., Vol. 68, pp 459-475, and Vol. 72, pp. 465-474). The process starts with a plasma provided by mixing various blood samples. The method involves a fractional precipitation under various conditions. In a first stage, fibrinogen is initially precipitated by the addition of 8 percent ethanol at a temperature of $-3°$ C at a pH of 7.2. The first precipitate is removed by filtration. A second precipitate, which comprises mainly gamma globulin, is formed from the supernatant phase by the addition of 19 percent ethanol at a pH of 5.6. The second precipitate (designated as Cohn-fraction II-III is recovered by filtration and is purified by redesolving the precipitate and thereafter rerecipitating at a pH of 5 with 8 percent ethanol to obtain a second fibrinogen precipitate which is removed by filtration. The remaining supernatant phase is again precipitated with 25 percent ethanol at a pH of 7.2. The resulting precipitate contains at least 90 percent gamma globulin. The gamma globulin precipitate is recovered, dissolved in a suitable buffer solution and is subjected to sterile filtration. The gamma globulin is then ready for use by humans.

While the Cohn Method produces gamma globulin preparations which are suitable for many uses, it has been found that in numerous instances, gamma globulin prepared by the Cohn Method has an anti-complementary activity such that complications result from reaction of the body in the case of intravenous application.

Accordingly, numerous methods have been proposed or attempted to increase or improve the intravenous compatibility of gamma globulins. For example, the following methods or processes are known:
1. Treatment with suitable enzymes;
2. Hydrolysis at high hydrogen ion concentration (e.g. at a pH of 4.0); and
3. Modification by means of beta propiolactone.

However, it has been found that the known processes for improving gamma globulin intravenous compatibility tend to modify the gamma globulin molecule and to cause variation in the chemical structure to such degree that the activity is reduced and the average retention time is shortened.

Accordingly, it is a principal object of the present invention to provide a process for increasing or improving the intravenous compatibility of gamma globulin, which process avoids the disadvantages of prior known processes and provides the following improvements:

- the structure of the gamma globulin molecule is varied to minimum degree;
- the anti complementary activity is greatly reduced as compared with conventional gamma globulin operations;
- the retention period in the organism is increased and the gamma globulin preparation is more compatible than conventional preparations.

It is another object of the present invention to provide a process for separating, intact, a gamma globulin molecule from damaged gamma globulin molecules to provide a further improvement in purity and compatibility of gamma gobulin for intravenous administration.

These and other objects of the present invention will become more apparent from the following detailed description and the accompanying drawings wherein.

Figure 1:
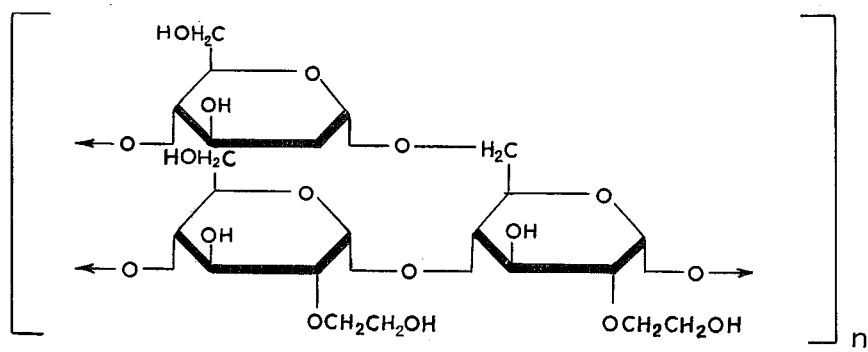
FIG. 1 is a structural formula of hydroxyethyl starch.

In general, in accordance with the process of the present invention for providing gamma globulin with improved intravenous compatibility, the gamma globulin precipitated from blood or from blood products is dissolved in an aqueous solution containing a hydrocolloid. A first fraction of undesirable materials is precipitated from the solution and is separated from the solution by any suitable method, such as centrifugation. A second fraction consisting substantially of desirable gamma globulin is then precipitated from the aqueous solution containing the hydrocolloid. The gamma globulin can then be recovered by any suitable method, such as centrifugation. Preferably, the gamma globulin is then redissolved in a physiological normal saline solution for use in intravenous applications. While not intending to be bound by any theory, it is believed that the hydrocolloid molecules protect and shield the globulin molecules from each other and aid to displace these molecules from the solution during the subsequent precipitation step. As used herein, the term "hydrocolloid" refers to any of those colloidal substances which have affinity for water and more capable of forming lyophilic sols. Preferred hydrocolloids are selected from the group consisting of hydroxyethyl starch (HES), dextrose, albumin, polyalcohols and polyvinyls.

In a further embodiment of the present invention, the gamma globulin produced by the above process is provided with still higher quality and purity by mixing the aqueous solution containing the gamma globulin and hydrocolloid with a slurry or suspension of a clay mineral prior to precipitating the first and second fractions, as described hereinabove. As used herein, the term "clay mineral" refers to hydrosilicates of aluminum, iron, magnesium or potassium. Particularly, preferred clay minerals are stratified micaceous silicates, such as montmorillonite minerals, kaolin minerals and the illite-bravaisite-hydromica group of minerals. Nonstratified clay minerals such as attapulgite and sepiolite can also be used. This preferred embodiment of the invention will be described more fully hereinafter.

More particularly, in the process of the invention, the gamma globulin obtained from blood or blood products by any known method is introduced into a buffered solution containing a hydrocolloid. A particularly preferred hydrocolloid is hydroxyethyl starch, however, a similar effect is provided by use of the other hydrocolloids capable of forming lyophilic sols, such as gelatin, dextrous, albumin, polyalcohols and polyvinyls. The pH of the buffered solution is preferably within the range of from about 3.5 to about 8.0. A particularly preferred pH range is from about 6.5 to about 6.9.

The level of hydrocolloid in the aqueous solution may range from between about 1 and about 30 percent; a preferred range for use of the hydrocolloid is at a level of from about 8 to about 10 percent. All percentages used herein are by weight unless otherwise specifically indicated.

As indicated, hydroxyethyl starch is a particularly preferred hydrocolloid. The hydroxyethyl starch preferably has a molecular weight of between 1000 and 900,000.

After the gamma globulin is dissolved in the buffered solution containing the hydrocolloid, a first undesirable fraction of the gamma globulin is precipitated by adding an organic solvent to the buffered solution. Any suitable organic solvent can be used, such as the $C_1$-$C_4$ aliphatic alcohols, ketones, aldehydes and glycols and the polyglycols. A particularly preferred organic solvent for effecting the precipitation is polyethylene glycol.

The first fraction of undesired gamma globulin is precipitated from the buffered hydrocolloid solution by the addition of from about 8 to about 12 percent, preferably about 10 percent of the organic solvent. The first fraction is removed from the buffered solution of gamma globulin by centrifugation, or any other suitable method. The supernatant fluid, after centrifugation, is mixed with additional organic solvent at a level of from about 16 to about 24 percent, preferably about 20 percent. The pH of the supernatant phase is preferably at a level of from about 7.0 to about 7.2. A second fraction, which is substantially pure gamma globulin, is precipitated after the higher level of organic solvent is added to the buffered solution. The gamma globulin is then recovered by centrifugation.

The precipitate of gamma globulin recovered by centrifugation from the buffered solution may then be dissolved in a physiological normal saline solution and adjusted to a desired concentration. A typical concentration for intravenous injection is about 5 percent. After sterile filtration the solution is ready for therapeutic use.

In a further embodiment of the invention, the quality and purity of the gamma globulin is improved by adding a slurry or suspension of a clay mineral to the aqueous solution of gamma globulin and the hydrocolloid prior to precipitating the first fraction and the second fraction. The clay mineral is preferably present in the slurry at a level sufficient to provide from about 0.2 to about 10 percent by weight of the clay mineral in the mixture of the aqueous solution of the slurry.

After allowing a sufficient period of reaction time to pass, usually from about 2 to about 10 hours or overnight, a precipitant such as the aforementioned organic solvents is added to the aqueous solution to cause precipitation of a first undesirable fraction of gamma globulin. The undesirable gamma globulin fraction and the clay mineral is then separated from the mixture by centrifugation. The supernatant phase is then treated with additional organic solvent at a level of from about 16 to about 24 percent to recover a second gamma globulin fraction of extremely high quality and high purity.

As indicated, preferred clay minerals are stratified micaceous silicates. Such silicates are characterized by clay minerals which have 2-layer crystal lattices, which are a sheet of silica tetrahedra and an alumina-Gibbsite sheet. Adjacent cells are spaced and the inter planar spacing normal to the (001) cleavage are the most significant critera used in x-differentiation between the clay mineral groups.

A typical analysis of kaolin minerals is set forth hereinbelow in Table I.

TABLE I

| Component | 1 | 2 | 3 | 4 | 5 | 6 | 7 |
|---|---|---|---|---|---|---|---|
| $SiO_2$, % | 45.44 | 52.46 | 40.26 | 46.5 | 45.78 | 42.68 | 44.90 |
| $Al_2O_3$, % | 38.52 | 32.20 | 37.95 | 39.5 | 36.46 | 38.49 | 38.35 |
| $Fe_2O_3$, % | 0.80 | 1.69 | 0.30 | — | 0.28 | 1.55 | 0.43 |
| FeO, % | — | — | — | — | 1.08 | — | — |
| MgO, % | 0.08 | None | — | — | 0.04 | 0.08 | Trace |
| CaO, % | 0.08 | 0.03 | 0.22 | — | 0.50 | — | Trace |
| $K_2O$, % | 0.14 | 0.31 | 0.74 | — | 0.25 | 0.49 | 0.28 |
| $Na_2O$, % | 0.66 | 0.25 |  | — |  | 0.28 | 0.14 |
| $TiO_2$, % | 0.16 | 0.55 | — | — | — | 2.90 | 1.80 |
| $H_2O$, % removed at 105° C. | 0.60 | 1.38 | 4.45 | — | 2.05 | — | — |
| $H_2O$, % removed at higher temp. | 13.60 | 12.07 | 15.94 | 14.0 | 13.40 | 14.07 | 14.20 |
| Total | 100.08 | 100.94 | 99.86 | 100.0 | 99.84 | 100.54 | 100.10 |

1. Kaolinite, Roseland, Va
2. Anauxite, near Lancha Plana, Calif.
3. Halloysite, Huron Co., Ind.
4. Theoretical kaolinite.
5. Washed kaolin, Webster, N.C.
6. Flint fire clay, near Owensville, Mo.
7. Typical sedimentary Kaolin, S.C., Ga., Ala. Courtesy of S. C. Lyons Typical formulae of the montmorillonite minerals are set forth hereinbelow in Table II.

| | |
|---|---|
| Montmorillonite | $[Al_{1.67}Mg_{0.33}(Na_{0.33})]Si_4O_{10}(OH)_2$ |
| Beidellite | $Al_{3.17}[Al_{0.33}(Na_{0.33})Si_{3.17}]O_{10}(OH)_2$ |
| Nontronite | $Fe^{3+}_{2.00}[Al_{0.33}(Na_{0.33})Si_{3.67}]O_{10}(OH)_2$ |
| Hectorite | $[Mg_{2.67}Li_{0.33}(Na_{0.33})]Si_4O_{10}(OH)_2$ |
| Saponite | $Mg_{3.00}[Al_{0.33}(Na_{0.33})Si_{3.67}]O_{10}(OH)_2$ |
| Sauconite | $[Zn_{1.48}Mg_{0.14}Al_{0.74}Fe^{3+}_{0.40}] [Al_{0.99}Si_{3.01}]$ |

-continued $$O_{10}(OH)_2X_{0.33}$$

Typical chemical analyses of the montmorillonite minerals are set forth hereinbelow in Table III.

TABLE III.

| Component | 1 | 2 | 3 | 4 | 5 | 6 |
|---|---|---|---|---|---|---|
| $SiO_2$, % | 51.14 | 47.28 | 43.51 | 55.86 | 42.99 | 34.46 |
| $Al_2O_3$, % | 19.76 | 20.27 | 2.94 | 0.13 | 6.26 | 16.95 |
| $Fe_2O_3$, % | 0.83 | 8.68 | 28.62 | 0.03 | 1.83 | 6.21 |
| FeO, % | — | — | 0.99 | — | 2.57 | — |
| MnO, % | Trace | — | — | None | 0.11 | — |
| ZnO, % | 0.10 | — | — | — | — | 23.10 |
| MgO, % | 3.22 | 0.70 | 0.05 | 25.03 | 22.96 | 1.11 |
| CaO, % | 1.62 | 2.75 | 2.22 | Trace | 2.03 | — |
| $K_2O$, % | 0.11 | Trace | — | 0.10 | Trace | 0.49 |
| $Na_2O$, % | 0.04 | 0.97 | — | 2.68 | 1.04 | — |
| $Li_2O$, % | — | — | — | 1.05 | — | — |
| $TiO_2$ % | None | — | — | None | — | 0.24 |
| $P_2O_5$ % | — | — | — | — | — | — |
| F, % | — | — | — | 5.96 | — | — |
| $H_2O$, % removed at 150° C. | 14.81 | 19.72 | 14.05 | 9.90 | 13.65 | 6.72 |
| $H_2O$, % removed at higher temp. | 7.99 | | 6.62 | 2.24 | 6.85 | 10.67 |
| Total | 99.75 | 100.37 | 100.02 | 102.98 100.47 O-F | 100.29 | 99.95 |

1. Montmorillonite, Montmorillon, France
2. Beidellite, Beidell, Colo.
3. Nontronite, Woody, Calif.
4. Hectorite, Hector, Calif.
5. Saponite, Ahmeek Mine, Mich.
6. Sauconite, Friedensville, Pa.

The illite-bravaisite-hydromica group of clay minerals consist of potassium-bearing clay minerals. The formula of illite has been expressed as

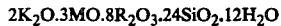

A typical formula for bravaisite is

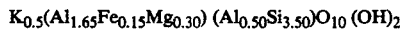

A representative chemical analysis of illite (the fine colloid fraction, Pennsylvanian underclay, near Fithian, Vermilion County, Ill.) is 51.22% $SiO_2$, 25.91% $Al_2O_3$ 4.59% Fe O 1.70% FeO, 2.84% MgO, 0.16% CaO, 0.17% $Na_2O$, 6.09% $K_2O$, 0.53% $TiO_2$ Attapulgite clay mineral is unique among the clay minerals in that its lattice structure is chain-like and dissimilar to the mica like sheets of the proceeding clay mineral groups. It is a magnesium-clay and a representative analysis is 55.03% $SiO_2$, 10.24% $Al_2O_3$, 3.53% $Fe_2O_3$ 10.49% MgO, 0.47% $K_2O$, 9.73% $H_2O$ Sepiolite is a fibrous, hydrated magnesium silicate mineral bearing similarities to attapulgite.

The gamma globulin obtained by the process of the present invention contains both damaged (broken) and undamaged or intact molecules. The damaged molecules are capable of forming hydrogen ion bonds. It is believed that the damaged molecules are deposited or bonded to greater degree within the silicate strata than are the undamaged or intact molecules. The intact gamma globulin molecules are left in the solution and are recovered after separation of the clay mineral from the solution. The damaged gamma globulin molecules, however, are bonded within the strata of the stratified micaceous silicates or on the crystal lattice of chain-like clay minerals and are easily removed from the solution by a suitable method, such as centrifugation.

The suitability of a clay mineral for use in this embodiment of the present invention is dependent upon the cation exchange capacity of the clay mineral. Clay minerals suitable for the purification process have a stratified or chain-like structure and have cations between the silicate strata or in the chain. In general, those clay minerals having a cation exchange capacity of from about 10 to about 100 me per 100 grams of air dried clay are suitable.

The silicates are used at a level of from about 0.2 to about 5 percent by weight of silicate based on the weight of the aqueous solution of gamma globulin and the hydrocolloid.

The reaction between the gamma globulin and the silicate preferably takes place within a temperature range of from about 4 to about 20° C and at a pH of between 4.0 and 7.6. The time of reaction is preferably within the range of from about 2 to about 10 hours. Preferably, the process is carried out overnight, since the reaction proceeds relatively slowly and an extended period of time provides improved result. Separation of the clay mineral containing the damaged molecule from the reaction mixture is preferably performed by centrifugation. However, other known separation methods may be used, such as filtration.

The following exmples further illustrate the various features of the invention, but are intended to in no may limit the scope of the invention which is defined in the appended claims.

EXAMPLE I

Gamma globulin is recovered from a blood sample collected from various sources by the Cohn method. Ethanol is added to the blood sample at a level of 8 percent to precipitate a first fraction (designated as Cohn Fraction I) at a pH of 7.2 and a temperature of −3° C. The first fraction is separated from the blood sample by centrifugation and the supernatant liquid is mixed with 19 percent of ethanol at a temperature of −5° C and a pH of 5.8. A second fraction (designated as Cohn Fraction II-III) is precipitated and is recovered by centrifugation. The second fraction consists primarily of gamma globulin. The second fraction is re-dissolved in water and a first fraction is again precipitated at a pH of 5 with 8 percent of ethanol. The first fraction is removed by centrifugation and the supernatant phase is again precipitated with 25% of ethanol at a pH of 7.2. The precipitate is recovered by centrifugation and this precipitate (Fraction II) comprises at least 90 percent of gamma globulin. This is gamma globulin obtained by the Cohn method.

The process of the invention is then used to reduce the anti-complementary activity. The gamma globulin precipitate obtained by the Cohn method is dissolved in a buffered aqueous solution at a pH of 6.7 at a concentration of 6 percent. The buffered aqueous solution contains 10 percent of hydroxyethyl starch. Polyethylene glycol is added to the dissolved gamma globulin at a level of 10 percent. A first precipitate is obtained which is removed by centrifugation. To the remaining supernatant phase is added 20 percent of polyethylene glycol at a pH of 7.2 to provide a second precipitate. The second precipitate is recovered by centrifugation. The recovered precipitate is the improved gamma globulin of the invention.

The gamma globulin is added to a physiologically normal saline solution at a level of 5.2 percent and is subsequently filtered under sterile conditions. The gamma globulin precipitate is then ready for therapeutic use.

Figure 2:
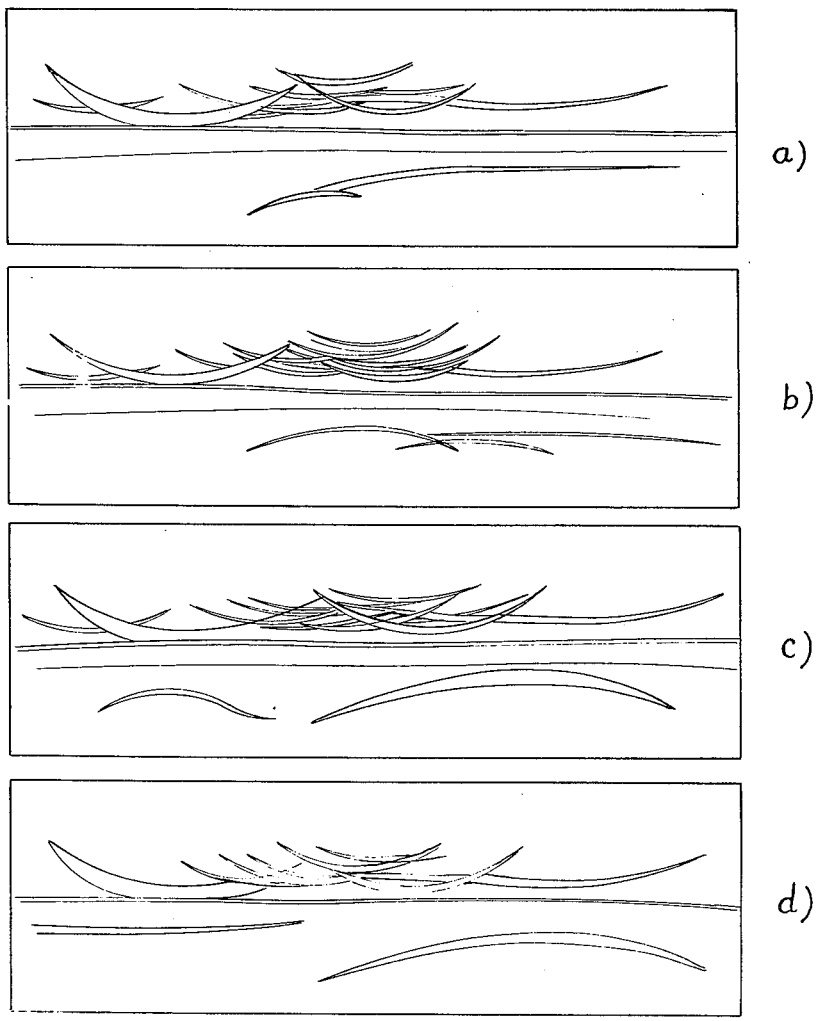
FIG. 2 is a series of immune electrophoresis diagrams of normal blood serum and of various gamma globulins which have been prepared in accordance with conventional processes and in accordance with the process of the present invention.

FIG. 1 shows the structural formula of hydroxyethyl starch. FIG. 2 is a series of immune electrophoresis diagrams (IEP) of various gamma globulins and of normal blood serum. The upper half of the diagrams of FIG. 2 show IEP diagrams of normal blood serum, whereas the lower half show IEP diagrams of:

(a) standard gamma globulin prepared by the Cohn method,
(b) gamma globulin modified by a proteolytic enzyme,
(c) gamma globulin modified by beta-propiolactone, and
(d) gamma globulin prepared in accordance with the process of the present invention.

Samples (a) to (c) each represent a commercially available gamma globulin. In addition to the gamma globulin (elongated crescent-shaped line in the right-hand portion of the diagram), these samples also show additional albumin or protein components of the human blood. The gamma globulin line of samples (a) and (b) are blurred because of the chemical modification of the gamma globulin. Sample (c) exhibits a varied position as compared with the gamma globulin line of the control blood serum.

In contrast, it is clearly evident that sample (d) which is prepared in accordance with the present invention consists substantially of pure gamma globulin. This is evident by the distinct crescent shaped line of the spectrum present in the normal blood serum.

It can be concluded from the diagrams that the gamma globulin contained by the process of the present invention has a purity of substantially 100 percent, since it corresponds substantially completely to the gamma globulin of the original blood serum. This means that the molecules are not substantially modified or chemically varied. These characteristics provide the advantageous properties of gamma globulin prepared in accordance with the process of the invention. These advantageous properties have been verified by tests, namely the positive intravenous compatibility and the greatly reduced anti-complementary activity to intracorporeal anti-bodies. These properties are clearly demonstrated by in-vitro tests. Gamma globulin prepared in accordance with the invention has also shown a particularly high storage stability.

EXAMPLE II

Gamma globulin is further improved in quality and purity by a further embodiment of the present invention. Gamma globulin obtained by the above described Cohn method is introduced into a buffered aqueous solution having a pH of 7.0 at a concentration of 6 percent. The buffered solution contains about 10 percent of hydroxyethyl starch. Thereafter, an aqueous slurry of bentonite SF is added to the solution. The bentonite contains primarily montmorillonite having a grain size of less than 80 microns and the manufacture is Feinbiochemika of Heidelburg, West Germany. The aqueous slurry contains sufficient bentonite to provide 2.5 percent by weight of bentonite in the aqueous buffered solution. The mixture is agitated thoroughly and is allowed to stand for 6 hours at a temperature of 15° C $\pm$ 2° C. Following this, polyethylene glycol is added to the solution at a level of 10 percent to precipitate a first fraction which is believed to be bonded to the bentonite. The bentonite together with the first fraction is then removed from the solution by centrifugation.

The supernatant liquid obtained from the preceding centrifugation step contains the desirable intact gamma globulin molecules. The supernatant liquid is adjusted to a pH of 7.2 by the addition of 0.1 M NaOH and the gamma globulin is recovered by the addition of 20 percent of polyethylene glycol. A precipitate of pure gamma globulin settles in the supernatant fluid. The precipitate is recovered by centrifugation and is added to a physiologically normal saline solution at a concentration of 5.2 percent. The solution is subjected to sterile filtration and the gamma globulin is then ready for therapeutic use.

EXAMPLE III

The method of the invention is used to recover a gamma globulin fraction with improved quality and purity utilizing a different clay mineral. The method of Example II is used with the exception that the aqueous solution contains 5 percent by weight of vermiculite. The solution is allowed to stand for 8 hours at a temperature of 15° C $\pm$ 2° C. After the addition of 10 percent by weight of hydroxyethyl starch, the vermiculite and a first gamma globulin fraction is removed by centrifugation. A pure gamma globulin fraction is then recovered as described by the method of Example II.

Immune electrophoresis diagrams have been used to determine that the yield of pure gamma globulin is increased by the use of the clay mineral described in Example II and III. The gamma globulin recovered is not modified or chemically varied. The gamma globulin has absolute compatibility when administered intravenously and does not show any substantial anti-complementary properties or characteristics.

Furthermore, the gamma globulin prepared by the method of the invention utilizing a clay mineral, possesses a high degree of stability which is verified by storage tests.

What is claimed is:

1. A process for preparing gamma globulin with improved intravenous compatibility comprising dissolving gamma globulin precipitated from blood or blood products in an aqueous solution containing a hyrocolloid, said hydrocolloid being capable of forming a lyophilic sol and said hydrocolloid being present at a level of from about 1 to about 30 percent by weight, precipitating and separating a first gamma globulin fraction containing undesirable materials from said solution by addition of an organic solvent thereto at a level of from about 8 to about 12 percent by weight, and thereafter precipitating a second gamma globulin fraction from said supernatant liquor of said first precipitation by addition of an organic solvent thereto at a level of from about 16 to about 24 percent by weight to obtain gamma globulin having improved intravenous compatibility, said aqueous solution containing said hydrocolloid being buffered and having a pH of from about 3.5 to about 8.0

2. A process in accordance with claim 1 wherein said hydrocolloid is selected from group consisting of hydroxyethyl starch, gelatin, dextrose, albumin, polyalcohols and polyvinyls.

3. A process in accordance with claim 2 wherein said hydrocolloid is hydroxyethyl starch.

4. A process in accordance with claim 1 wherein said pH is about 6.5 to about 6.9.

5. A process in accordance with claim 1 wherein said hydrocolloid is present in said aqueous solution at a level of from about 8 to about 10 percent.

6. A process in accordance with claim 3 wherein said hydroxyethyl starch is present in said aqueous solution at a level of from about 1 to about 30 percent.

7. A process in accordance with claim 1 wherein said hydrocolloid is hydroxyethyl starch which is present in said aqueous solution at a level of from about 1 to about 30 percent.

8. A process in accordance with claim 7 wherein said hydroxyethyl starch is present in said aqueous solution at a level of from about 8 to about 10 percent by weight.

9. A process in accordance with claim 3 wherein the molecular weight of said hydroxyethyl starch is within the range of from about 1000 to about 900,000.

10. A process in accordance with claim 1 wherein said aqueous solution further contains a silicate clay mineral.

11. A process in accordance with claim 10 wherein said clay mineral is hydrosilicate of aluminum, iron, magnesium or potassium selected from the group consisting of montmorillonite minerals, kaolin minerals, the illite-bravisitehydromica group of minerals, attapulgite and sepiolite.

12. A process in accordance with claim 10 wherein said silicate clay mineral is a stratified micaceous silicate.

13. A process in accordance with claim 10 wherein said clay mineral has a cation exchange capacity of from about 10 to about 100 me per 100 grams of air dried clay.

14. A process in accordance with claim 10 wherein said clay mineral is present in said aqueous solution at a level of from about 0.2 to about 5 percent by weight of clay mineral based on the weight of said aqueous solution.

15. A process in accordance with claim 10 wherein said clay mineral is bentonite.

16. A process in accordance with claim 10 said clay mineral is batevite.

17. A process in accordance with claim 10 wherein said clay mineral is vermiculite.

18. A process in accordance with claim 10 wherein said gamma globulin is reacted with said clay mineral at a temperature of from about +4 to about 20° C.

19. A process in accordance with claim 18 wherein the pH of said solution is from about 4.0 to about 7.6.

20. A process in accordance with claim 10 wherein said gamma globulin is reacted with said clay mineral for a period of from about 2 to about 10 hours.

* * * * *

UNITED STATES PATENT AND TRADEMARK OFFICE
CERTIFICATE OF CORRECTION

PATENT NO. : 4,126,605

DATED : November 21, 1978

INVENTOR(S) : Schneider et al.

It is certified that error appears in the above-identified patent and that said Letters Patent are hereby corrected as shown below:

Column 4, line 16, "of the slurry" should read --and the slurry--.

Column 9, line 17, the period is omitted at the end of the claim.

Signed and Sealed this

Twenty-sixth Day of February 1980

[SEAL]

Attest:

SIDNEY A. DIAMOND

Attesting Officer — Commissioner of Patents and Trademarks